United States Patent
Wang et al.

(10) Patent No.: US 12,121,498 B2
(45) Date of Patent: *Oct. 22, 2024

(54) ALLOSTERIC ENHANCING COMPOUND OF GABAA RECEPTOR AND PREPARATION AND USE THEREOF

(71) Applicant: XI'AN LIBANG ZHAOXIN BIOTECHNOLOGY CO., LTD., Xi'an (CN)

(72) Inventors: Rutao Wang, Xi'an (CN); Long An, Xi'an (CN); Yi Zhao, Xi'an (CN); Jinghua Pang, Xi'an (CN); Tao Chen, Xi'an (CN); Weijiao Wang, Xi'an (CN)

(73) Assignee: XI'AN LIBANG ZHAOXIN BIOTECHNOLOGY CO., LTD, Xi'an (CN)

( * ) Notice: Subject to any disclaimer, the term of this patent is extended or adjusted under 35 U.S.C. 154(b) by 502 days.

This patent is subject to a terminal disclaimer.

(21) Appl. No.: 17/271,852

(22) PCT Filed: Jul. 10, 2019

(86) PCT No.: PCT/CN2019/095393
§ 371 (c)(1),
(2) Date: Feb. 26, 2021

(87) PCT Pub. No.: WO2020/042766
PCT Pub. Date: Mar. 5, 2020

(65) Prior Publication Data
US 2021/0315836 A1    Oct. 14, 2021

(30) Foreign Application Priority Data
Aug. 31, 2018    (CN) .......................... 201811010454.1

(51) Int. Cl.
| | | |
|---|---|---|
| A61K 31/05 | (2006.01) | |
| A61K 9/00 | (2006.01) | |
| A61P 25/08 | (2006.01) | |

(52) U.S. Cl.
CPC ............ *A61K 31/05* (2013.01); *A61K 9/0019* (2013.01); *A61P 25/08* (2018.01)

(58) Field of Classification Search
CPC .................................................. A61K 31/05
See application file for complete search history.

(56) References Cited

U.S. PATENT DOCUMENTS

| | | |
|---|---|---|
| 10,329,243 B2 | 6/2019 | Wang et al. |
| 2015/0352052 A1 | 12/2015 | Wang et al. |
| 2015/0376099 A1 | 12/2015 | Wang et al. |
| 2016/0108024 A1 | 4/2016 | Gallego Sala et al. |
| 2018/0141895 A1 | 5/2018 | Wang et al. |
| 2018/0185299 A1 | 7/2018 | Wang et al. |

FOREIGN PATENT DOCUMENTS

| | | | |
|---|---|---|---|
| CN | 101804043 A | | 8/2010 |
| CN | 104045552 A | | 9/2014 |
| CN | 105250316 A | | 1/2016 |
| EP | 2960225 A1 | | 12/2015 |
| EP | 3246304 A2 | | 11/2017 |
| JP | 2015067577 A | | 4/2015 |
| JP | 2015521633 A | | 7/2015 |
| JP | 2018503637 A | | 2/2018 |
| WO | WO 2016/112875 | * | 7/2016 |
| WO | 2017120507 A1 | | 7/2017 |

OTHER PUBLICATIONS

First Office Action issued on Jul. 5, 2022 for counterpart Chinese patent application No. 201811011320.1, 15 pages.
Search Report issued on Jul. 5, 2022 for counterpart Chinese patent application No. 201811011320.1, 4 pages.
Teocchi et al., "Hippocampal gene expression dysregulation of Klotho, nuclear factor kappa B and tumor necrosis factor in temporal lobe epilepsy patients," Journal of Neuroinflammation, May 2013, 7 pages.
First Office Action issued on Jul. 6, 2022 for U.S. Appl. No. 17/271,828, 12 pages.
First Office Action for counterpart Chinese Patent Application No. 201811010454.1, dated Feb. 16, 2022, 12 pages.
Nicholas P.Barwell et al., "A Synthetic Lectin for b-Glucosyl," Angew. Chem. Int. Ed., vol. 48, pp. 7673-7674, S3-S8 (2009).
First Office Action issued for corresponding Japanese Patent Application No. 2021-536132, dated Apr. 5, 2022, 6 pages.

(Continued)

*Primary Examiner* — Sahar Javanmard
(74) *Attorney, Agent, or Firm* — Hoffman Warnick LLC

(57) ABSTRACT

The present disclosure provides an allosteric enhancing compound of GABA$_A$ receptors or a prodrug thereof, a method for preparing the same, and use thereof. The compound is represented by formula (1), wherein R$_1$ and R$_2$ are each independently selected from isopropyl or n-propyl; and when R$_1$ is n-propyl, R$_2$ is not isopropyl.

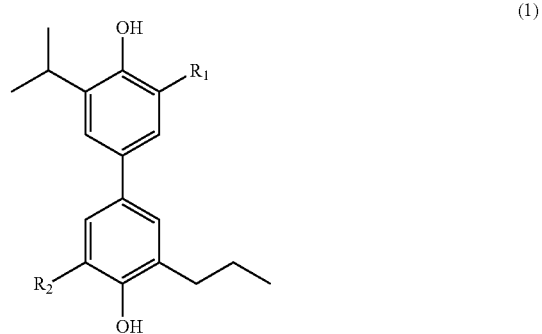

(1)

2 Claims, 1 Drawing Sheet

(56) References Cited

OTHER PUBLICATIONS

Search Report for counterpart Chinese Patent Application No. 201811010454.1, dated Feb. 16, 2022, 4 pages.
First Office Action issued for corresponding Japanese Patent Application 2021-536133 mailed on Apr. 26, 2022, 8 pages.
Extended European Search Report issued on Apr. 25, 2022 for counterpart European patent application No. 19856003.9, 7 pages.
Extended European Search Report issued on Apr. 28, 2022 for counterpart European patent application No. 19856387.6, 7 pages.
PCT International Search Report for International Application No. PCT/CN2019/095393, dated Sep. 26, 2019, 4 pages.

\* cited by examiner

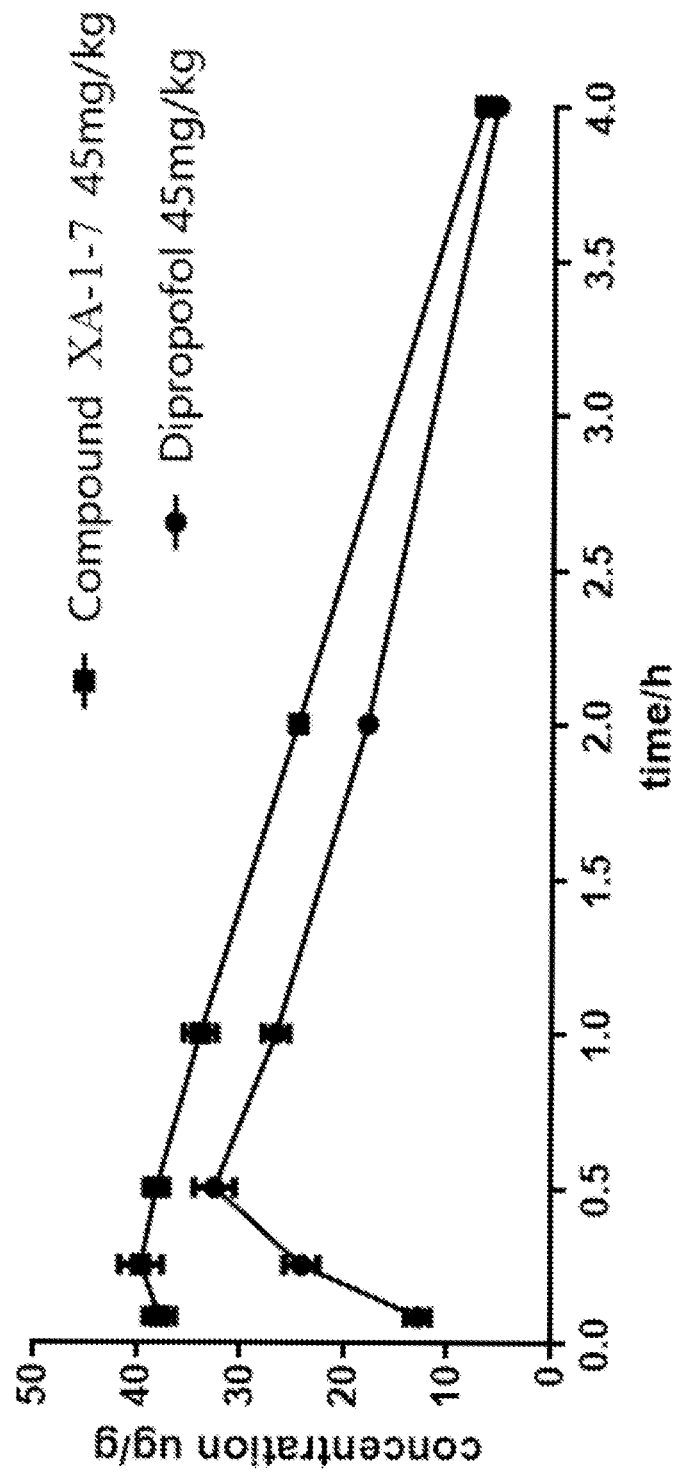

ALLOSTERIC ENHANCING COMPOUND OF GABAA RECEPTOR AND PREPARATION AND USE THEREOF

CROSS-REFERENCE TO RELATED APPLICATIONS

This application is a National Stage of International Application No. PCT/CN2019/095393, filed Jul. 10, 2019, which claims priority to Chinese Patent Application No. 201811010454.1, filed Aug. 31, 2018, both of which are hereby incorporated by reference in their entireties.

TECHNICAL FIELD

The present disclosure is directed to the field of pharmaceutical medicine, and in particular, to an allosteric enhancing compound of $GABA_A$ receptors, a method for preparing the same, and use thereof.

BACKGROUND ART

Epilepsy is a chronic disease in which sudden abnormal electrical discharges of neurons in the brain lead to transient brain dysfunction. Epileptic seizure refers to a clinical phenomenon caused by abnormal and excessive super-synchronized discharges of brain neurons. Epilepsy has become a health problem causing growing concerns to the society because of its increasing morbidity currently at home and abroad. Statistics show that epilepsy patients account for about 0.5% to 1% of the world's population. Despite the continuous and in-depth research on epilepsy, the pathogenesis of epilepsy remains poorly understood, and the drugs currently used can only partially relieve the conditions of epilepsy patients and show an efficacy rate of merely 60% to 70% on patients with progressive grand mal seizures.

In recent years, with the advances in studies of epilepsy, it has been found that $GABA_A$ receptors are closely related to the onset of epilepsy. $GABA_A$ receptors are the most important central inhibitory receptors in the human central tissue. Activation of $GABA_A$ receptors in the brain can hyperpolarize neurons and reduce the excitability of nerve cells. Traditional anti-epileptic drugs, benzodiazepines and barbiturates, and recently developed and marketed drugs such as sodium valproate and levetiracetam, are all related to enhancement of the effect of $GABA_A$ receptors or increase in tissue concentration of GABA.

Chinese patent No. ZL201010160034.9 discloses a dipropofol compound (3,3',5,5'-tetraisopropylbiphenyl-4,4'-diol), which is a novel type of allosteric modulating enhancer of $GABA_A$ receptors developed by Xi'an Libang Pharmaceutical Co., Ltd as a new anti-epileptic drug for treatment of various seizures including Status Epilepticus. Pre-clinical studies of this compound showed good anti-epileptic activity and less side effects, and the compound is now in clinical trials. However, in the pre-clinical studies, it was found that the compound entered the brain slowly after intravenous injection, took a certain period of time to reach a therapeutic threshold concentration in the brain, and cannot take effect quickly against epilepsy at onset. Therefore, the present disclosure aims to develop a fast-acting anti-epileptic drug with improved efficacy.

SUMMARY OF INVENTION

An objective of the present disclosure is to provide an allosteric enhancing compound of $GABA_A$ receptors or a prodrug thereof.

Another objective of the present disclosure is to provide a method for preparing the allosteric enhancing compound of $GABA_A$ receptors or a prodrug thereof.

Yet another objective of the present disclosure is to provide a pharmaceutical composition.

A further objective of the present disclosure is to provide use of the allosteric enhancing compound of $GABA_A$ receptors or a prodrug thereof or the pharmaceutical composition.

To achieve the above objectives, in one aspect, the present disclosure provides an allosteric enhancing compound of $GABA_A$ receptors or a prodrug thereof, wherein the compound is represented by formula (1):

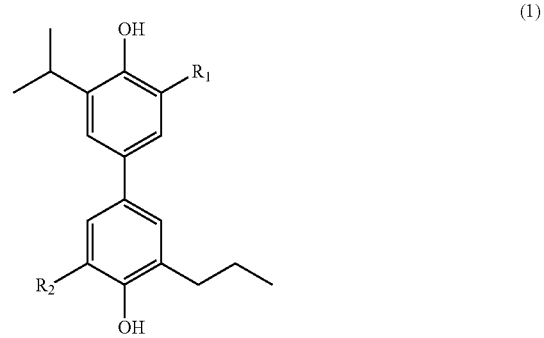

(1)

wherein $R_1$ and $R_2$ are each independently selected from isopropyl or n-propyl; and when $R_1$ is n-propyl, $R_2$ is not isopropyl.

According to some embodiments of the present disclosure, the enhancing compound is selected from the following structures:

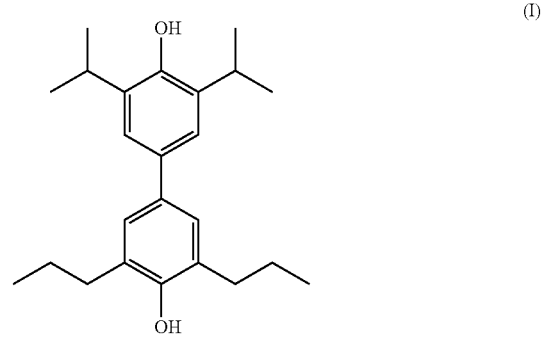

(I)

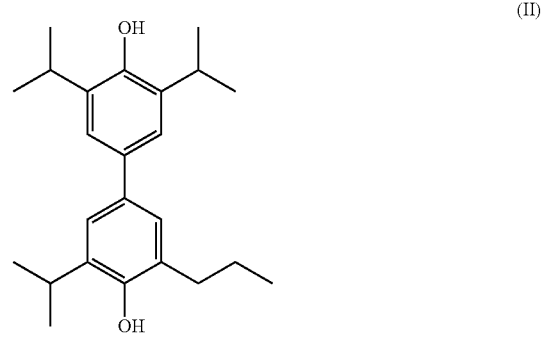

(II)

-continued (III)

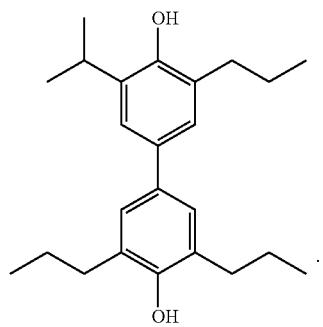

According to some embodiments of the present disclosure, the prodrug has a structure represented by Formula (2):

(2)

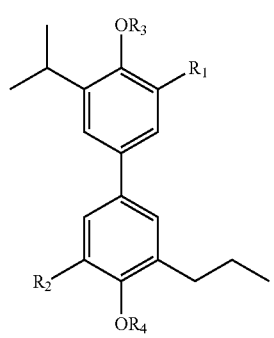

wherein $R^3$ and $R_4$ are each independently selected from

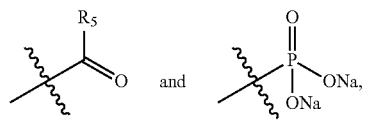

wherein $R_5$ is a $C_{1-4}$ alkyl.

In another aspect, the present disclosure also provides a method for preparing the allosteric enhancing compound of $GABA_A$ receptors or a prodrug thereof, wherein the method comprises, subjecting a borate ester-based compound (c) and a para-bromo monophenol compound (d) to a Suzuki coupling reaction to obtain the biphenyldiol compound (1):

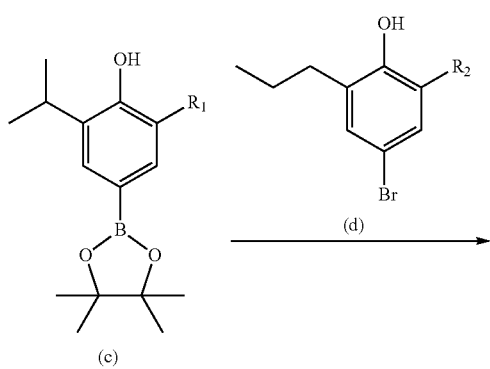

-continued

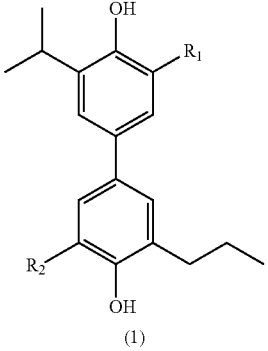

(1)

alternatively, the method comprises, subjecting a borate ester-based compound (c') and a para-bromo monophenol compound (d') to a Suzuki coupling reaction to obtain the biphenyldiol compound (1):

According to some embodiments of the present disclosure, the Suzuki coupling reaction between the borate ester-based compound (c) or (c') and the para-bromo monophenol compound (d) or (d') is carried out at a reaction temperature of 60 to 80° C.

According to some embodiments of the present disclosure, the Suzuki coupling reaction between the borate ester-based compound (c) or (c') and the para-bromo monophenol compound (d) or (d') is carried out for a reaction duration of 0.5 to 2 h.

According to some embodiments of the present disclosure, the method further comprises, preparing the borate ester-based compound (c) by a reaction between a bromo monophenol compound (b) and BPD (dichlorophenylphosphine):

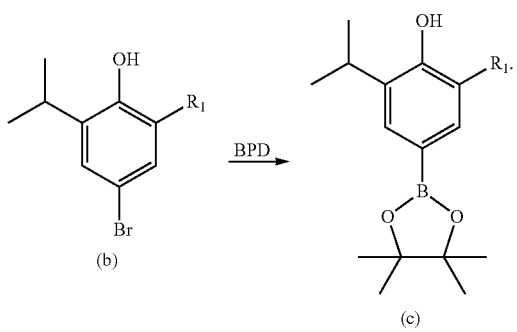

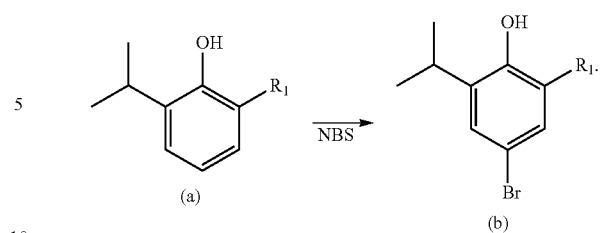

According to some embodiments of the present disclosure, the method further comprises, preparing the bromo monophenol compound (b') by a bromine substitution reaction of a compound of general formula (a') with NBS:

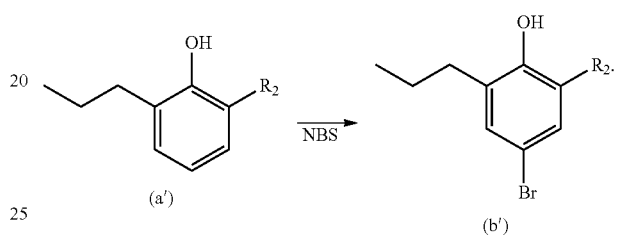

According to some embodiments of the present disclosure, the method further comprises, preparing the borate ester-based compound (c') by a reaction between a bromo monophenol compound (b') and BPD (dichlorophenylphosphine):

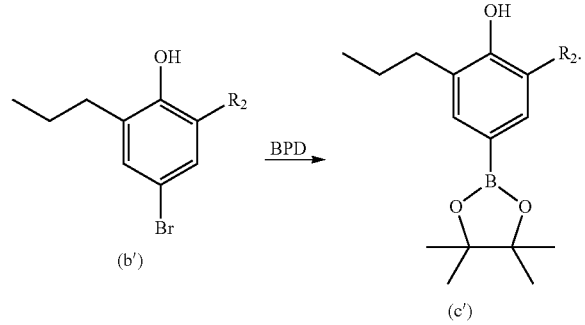

According to some embodiments of the present disclosure, the borate ester-based compound (c) is obtained by a reaction between the bromo monophenol compound (b) and BPD in the presence of a palladium catalyst.

According to some embodiments of the present disclosure, the borate ester-based compound (c') is obtained by a reaction between the bromo monophenol compound (b') and BPD in the presence of a palladium catalyst.

According to some embodiments of the present disclosure, the palladium is used in a catalytic amount.

According to some embodiments of the present disclosure, the reaction between the bromo monophenol compound (b) and BPD is carried out at a reaction temperature of 80 to 150° C.

According to some embodiments of the present disclosure, the reaction between the bromo monophenol compound (b) and BPD is carried out for a reaction duration of 10 to 24 h.

According to some embodiments of the present disclosure, the reaction between the bromo monophenol compound (b') and BPD is carried out at a reaction temperature of 80 to 150° C.

According to some embodiments of the present disclosure, the reaction between the bromo monophenol compound (b') and BPD is carried out for a reaction duration of 10 to 24 h.

According to some embodiments of the present disclosure, the method further comprises, preparing the bromo monophenol compound (b) by a bromine substitution reaction of a compound of general formula (a) with NBS:

According to some embodiments of the present disclosure, the bromo monophenol compound (b) is obtained by a bromine substitution reaction of a compound of general formula (a) with NBS in acetonitrile as the reaction solvent.

According to some embodiments of the present disclosure, the bromo monophenol compound (b') is obtained by a bromine substitution reaction of a compound of general formula (a') with NBS in acetonitrile as the reaction solvent.

According to some embodiments of the present disclosure, the bromine substitution reaction of a compound of general formula (a) with NBS is carried out at a reaction temperature of 20 to 30° C.

According to some embodiments of the present disclosure, the bromine substitution reaction of a compound of general formula (a) with NBS is carried out at room temperature.

According to some embodiments of the present disclosure, the bromine substitution reaction of a compound of general formula (a) with NBS is carried out for a reaction duration of 2 to 10 min.

According to some embodiments of the present disclosure, the bromine substitution reaction of a compound of general formula (a) with NBS is carried out for a reaction duration of 5 min.

According to some embodiments of the present disclosure, the bromine substitution reaction of a compound of general formula (a') with NBS is carried out at a reaction temperature of 20 to 30° C.

According to some embodiments of the present disclosure, the bromine substitution reaction of a compound of general formula (a') with NBS is carried out at room temperature.

According to some embodiments of the present disclosure, the bromine substitution reaction of a compound of general formula (a') with NBS is carried out for a reaction duration of 2 to 10 min.

According to some embodiments of the present disclosure, the bromine substitution reaction of a compound of general formula (a') with NBS is carried out for a reaction duration of 5 min.

In another aspect, the present disclosure also provides a pharmaceutical composition comprising a therapeutically effective amount of the allosteric enhancing compound of GABA$_A$ receptors or a prodrug thereof according to any embodiment of the present disclosure, and one or more pharmaceutically acceptable carriers and/or excipients.

In yet another aspect, the present disclosure also provides a method for promoting sedation and hypnosis, protecting the brain, or treating and/or preventing anxiety, depression, insomnia, nausea, vomiting, migraine, schizophrenia, convulsions and epilepsy in an animal or human, comprising administering to the animal or human the allosteric enhancing compound of GABA$_A$ receptors or a prodrug thereof according to the present disclosure, or the pharmaceutical composition according to the present disclosure.

In summary, the present disclosure provides an allosteric enhancing compound of GABA$_A$ receptors or a prodrug thereof, a method for preparing the same, and use thereof. The enhancing compound according to the present disclosure has the following advantages:

although having a target affinity similar to that of the dipropofol, the enhancing compound according to the present disclosure enters the brain tissue through the blood-brain barrier more easily than the dipropofol, thereby exerting better efficacy in animals.

DESCRIPTION OF DRAWINGS

FIG. 1 is a graph showing the changes in the concentration of Compound XA-1-7 and dipropofol in the brain tissue of rats at different time points after administration.

DETAILED DESCRIPTION OF INVENTION

The technical solutions of the present disclosure will be described in detail hereinafter with reference to the drawings and Examples, which are included in but do not limit the scope of protection of the present disclosure.

Example 1. Preparation of 3,5-diisopropyl-3',5'-dipropyl-biphenyl-4,4'-diol

Synthetic Route:

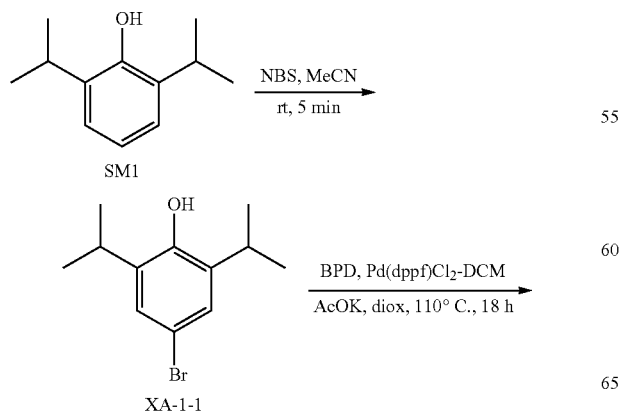

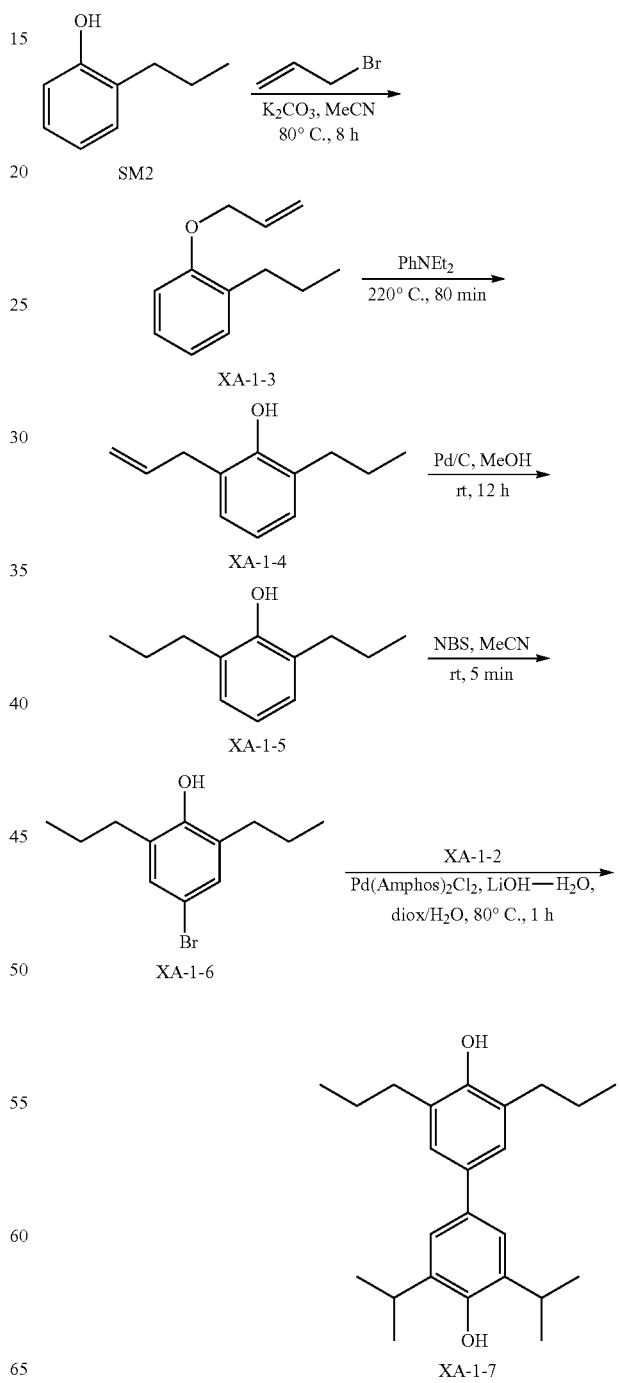

Step 1: 4-bromo-2,6-diisopropylphenol (XA-1-1)

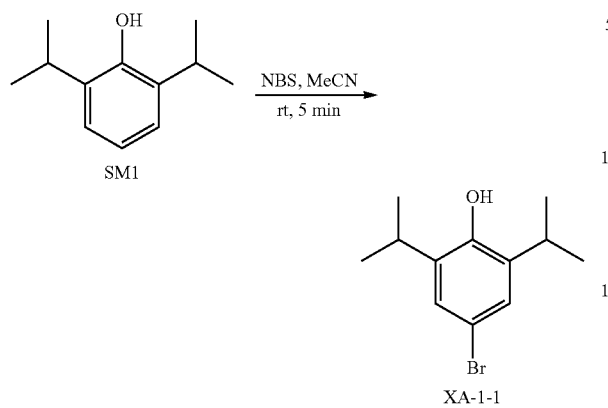

2,6-Diisopropylphenol (10.7 g, 60.1 mmol, 1.00 eq) was dissolved in anhydrous acetonitrile (120 mL), and NBS (10.7 g, 60.1 mmol, 1.00 eq) was added thereto under stirring. A reaction was allowed to proceed for 5 min under stirring, while monitored with spots on a TLC plate. After the reaction was complete, the reaction mixture was rotary-dried at a low temperature, and the resultant crude product was purified by column chromatography (petroleum ether/ethyl acetate=20:1, Rf-0.4) to obtain 13.8 g light yellow oil.

$^1$H NMR (500 MHZ, Chloroform) δ 7.21 (s, 1H), 3.73 (s, 1H), 3.05 (s, 1H), 1.14 (s, 6H).

Step 2: 2,6-diisopropyl-4-(4,4,5,5-tetramethyl-1,3,2-dioxaborolan-2-yl)phenol (XA-1-2)

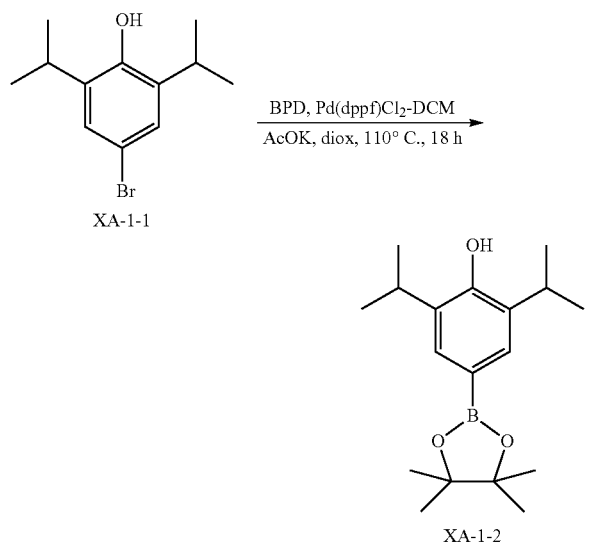

XA-1-1 (13.5 g, 52.5 mmol, 1.00 eq) was dissolved in dioxane/water (320 mL/32 mL), and then KOAc (25.7 g, 262.5 mmol, 5.00 eq), BPD (66.7 g, 262.5 mmol, 5.00 eq), and Pd(dppf)Cl$_2$ DCM complex (2.45 g, 3.00 mmol, 0.05 eq) were sequentially added thereto. The mixture was purged with nitrogen 5 times, stirred at room temperature for 5 minutes, and then heated and stirred at 110° C. for 18 h under nitrogen protection. The reaction was monitored with spots on a TLC plate until the reaction was complete. The reaction solution was rotary-dried. The resultant solid was diluted with ethyl acetate (300 mL), and washed with a saturated solution of sodium chloride (100 mL×3). The organic phase was dried over anhydrous sodium sulfate and rotary-dried. The resultant solid was purified by column chromatography (petroleum ether/ethyl acetate=10:1, Rf-0.5) to obtain 24.5 g light yellow solid.

$^1$H NMR (500 MHz, Chloroform) δ 7.02 (s, 2H), 3.12 (dtd, J=13.7, 6.7, 1.0 Hz, 2H), 1.39 (s, 12H), 1.24 (d, J=6.8 Hz, 12H).

Step 3: 1-(allyloxy)-2-propylbenzene (XA-1-3)

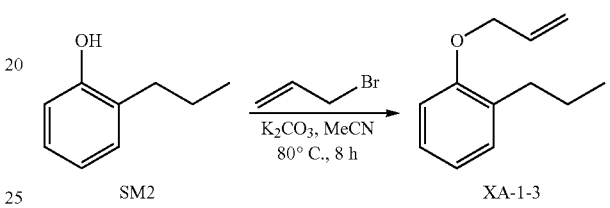

2-Propylphenol (2.72 g, 20.0 mmol, 1.00 eq) was dissolved in anhydrous acetonitrile (120 mL), to which allyl bromide (10.7 g, 30.0 mmol, 1.50 eq) and K$_2$CO$_3$ (5.52 g, 40.0 mmol, 2.00 eq) were added, followed by heating and stirring at 80° C. for 8 h. With the above reaction conditions, 4 batches of reactions in total were carried out. The reactions were monitored by LCMS until completion. The reaction solutions were combined, rotary-dried, diluted with ethyl acetate (200 mL), washed with a saturated solution of sodium chloride (60 mL×3), dried over anhydrous sodium sulfate, and purified by column chromatography (petroleum ether/ethyl acetate=15:1, Rf=0.5) to obtain 14.9 g colorless oil.

$^1$H NMR (500 MHZ, Chloroform) δ 7.07 (s, 1H), 6.77 (t, J=27.5 Hz, 3H), 6.06 (s, 1H), 5.37 (d, J=60.0 Hz, 2H), 4.68 (s, 2H), 2.63 (s, 2H), 1.64 (s, 2H), 0.94 (s, 3H).

Step 4: 2-allyl-6-propylphenol (XA-1-4)

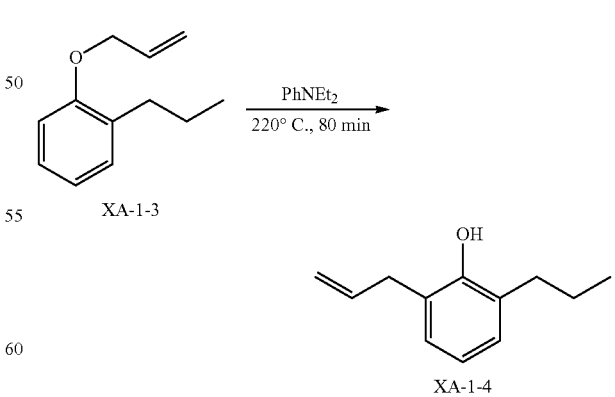

XA-1-3 (5.00 g, 28.4 mmol, 1.00 eq) was dissolved in PhNEt$_2$ (57 mL), purged with nitrogen 5 times, and refluxed for 80 minutes. The reaction was monitored by LCMS until it was completed. The reaction solution was diluted with ethyl acetate (200 mL), and washed with 1 M hydrochloric acid (60 mL) until PhNEt$_2$ disappeared (monitored with spots on a TLC plate). The organic phase was dried over anhydrous sodium sulfate, and rotary-dried, and the resultant solid was purified by column chromatography (petroleum ether/ethyl acetate=10:1, Rf-0.5) to obtain 3.7 g yellow oil.

$^1$H NMR (500 MHZ, Chloroform) δ 7.31-6.90 (m, 3H), 5.92 (s, 1H), 5.12 (s, 1H), 4.87 (s, 1H), 4.24 (s, 1H), 3.33 (s, 2H), 2.63 (s, 2H), 1.64 (s, 2H), 0.94 (s, 3H).

Step 5: 2,6-dipropylphenol (XA-1-5)

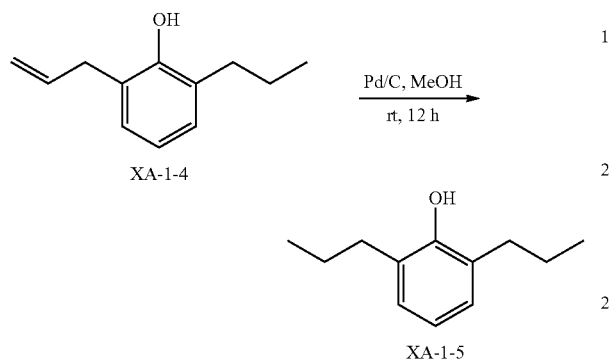

XA-1-4 (3.70 g, 21.0 mmol, 1.00 eq) was dissolved in MeOH (57 mL), purged with hydrogen 5 times, and stirred at room temperature under a hydrogen atmosphere for 12 h. The reaction was monitored by LCMS. A filter cake was obtained by filtration and washed with methanol (20 mL×2), and the filtrates were combined and rotary-dried to obtain 2.95 g yellow oil.

$^1$H NMR (500 MHz, Chloroform) δ 7.09 (s, 1H), 6.93 (s, 2H), 4.73 (s, 1H), 2.63 (s, 4H), 1.64 (s, 4H), 0.94 (s, 6H).

Step 6: 4-bromo-2,6-dipropylphenol (XA-1-6)

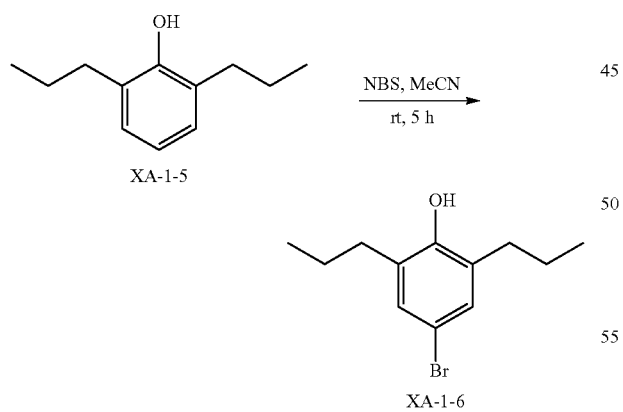

XA-1-5 (2.95 g, 16.6 mmol, 1.00 eq) was dissolved in anhydrous acetonitrile (35 mL), and NBS (2.95 g, 16.6 mmol, 1.00 eq) was added thereto under stirring, followed by stirring for 5 minutes. The reaction was monitored with spots on a plate. The reaction mixture was rotary-dried at a low temperature, and the crude product was purified by column chromatography (petroleum ether/ethyl acetate-20:1, Rf-0.4) to obtain 2.90 g light yellow oil.

$^1$H NMR (500 MHZ, Chloroform) δ 7.09 (s, 2H), 4.64 (s, 1H), 2.63 (s, 4H), 1.64 (s, 4H), 0.94 (s, 6H).

Step 7: 3,5-diisopropyl-3',5'-dipropyl-[1,1'-biphenyl]-4,4'-diol (XA-1-7)

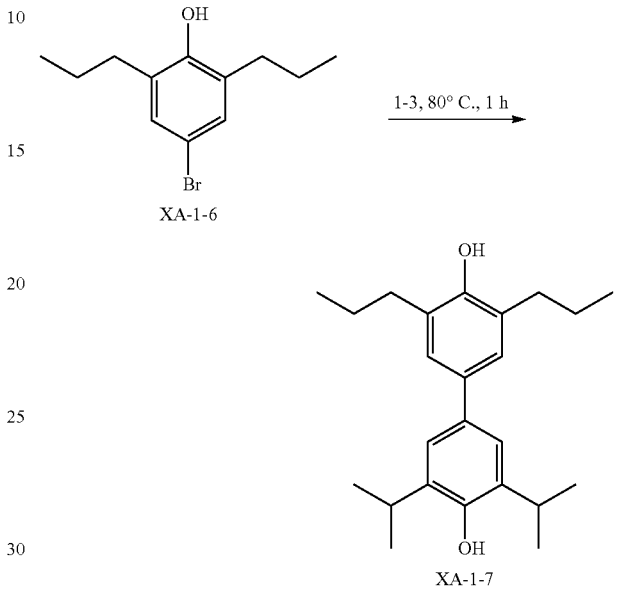

XA-1-6 (2.49 g, 9.80 mmol, 1.00 eq) was dissolved in dioxane/water (30 mL/15 mL), and LiOH—H$_2$O (823 mg, 19.6 mmol, 2.00 eq), XA-1-2 (4.47 g, 14.7 mmol, 1.5 eq), and Pd(Amphos)$_2$Cl$_2$ (372 mg, 0.49 mmol, 0.05 eq) were sequentially added thereto, purged with nitrogen 5 times, stirred at room temperature for 5 minutes, and then heated and stirred at 80° C. for 1 hour. The reaction was monitored by LCMS. The reaction solution was diluted with ethyl acetate (90 mL), and washed with a saturated solution of sodium chloride (30 mL×3). The organic phase was dried over anhydrous sodium sulfate, and rotary-dried. The crude product was purified by column chromatography (petroleum ether/ethyl acetate=10:1, Rf-0.4) to obtain 1.75 g yellow solid (purity ~90%), which was further purified by high-pressure preparative liquid phase chromatography to obtain 1.45 g yellow solid as the product.

$^1$H NMR (500 MHZ, Chloroform) δ 7.67 (s, 2H), 7.55 (s, 2H), 4.84 (s, 1H), 3.74 (s, 1H), 3.05 (s, 2H), 2.63 (s, 4H), 1.64 (s, 4H), 1.14 (s, 12H), 0.94 (s, 6H).

Example 2. Preparation of 3,3',5-triisopropyl-5'-propyl-biphenyl-4,4'-diol

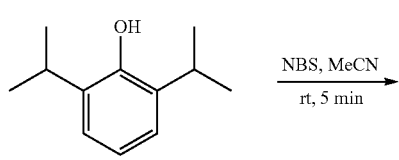

-continued

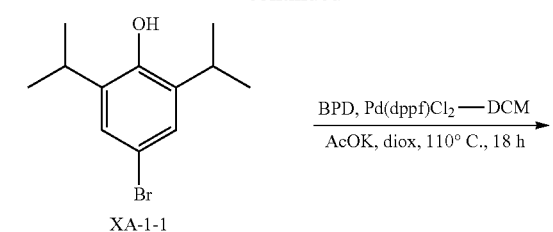

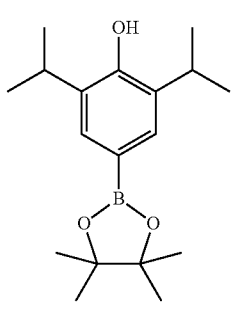

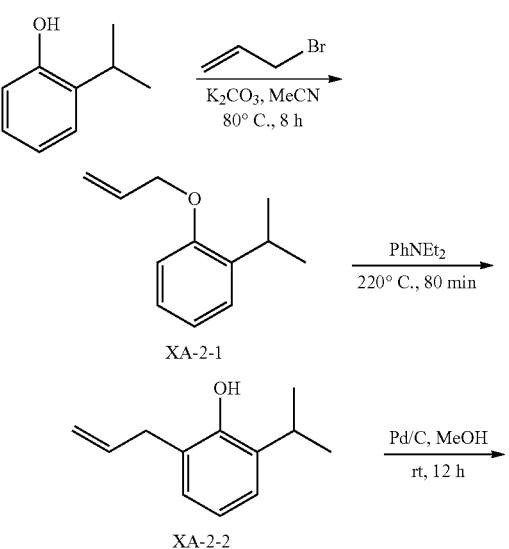

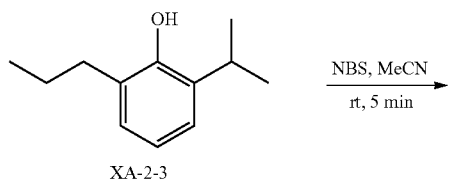

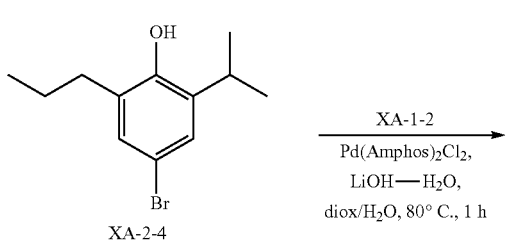

-continued

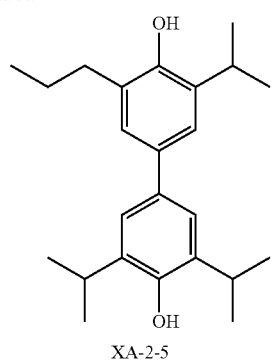

The steps for preparation of Compound XA-1-2 can be seen in Example 1.

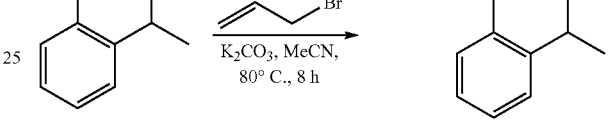

2-Isopropylphenol (10.88 g, 80.0 mmol, 1.00 eq) was dissolved in anhydrous acetonitrile (480 mL), allyl bromide (42.8 g, 120.0 mmol, 1.50 eq) and K$_2$CO$_3$ (22.08 g, 160.0 mmol, 2.00 eq) were added thereto, and heated and stirred at 80° C. for 8 h. The reaction was monitored by LCMS until completion. The reaction solutions were combined, rotary-dried, diluted with ethyl acetate (800 mL), washed with a saturated solution of sodium chloride (240 mL×3), dried over anhydrous sodium sulfate, and purified by column chromatography (petroleum ether/ethyl acetate=15:1, Rf=0.5) to obtain 59.6 g colorless oil.

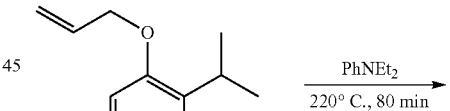

XA-2-1 (15.00 g, 85.2 mmol, 1.00 eq) was dissolved in PhNEt$_2$ (171 mL), purged with nitrogen 5 times, and refluxed for 80 minutes. The reaction was monitored by LCMS until completion. The reaction solution was diluted with ethyl acetate (600 mL), and washed with 1 M hydrochloric acid (160 mL) until PhNEt$_2$ disappeared (monitored with spots on a TLC plate). The organic phase was dried over anhydrous sodium sulfate and rotary-dried. The resultant solid was purified by column chromatography (petroleum ether/ethyl acetate=10:1, Rf=0.5) to obtain 11.1 g yellow oil.

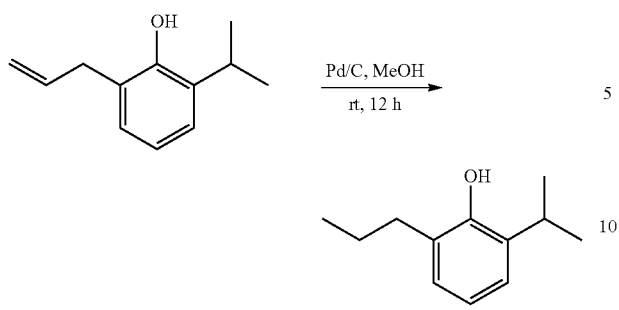

XA-2-2 (7.4 g, 42 mmol, 1.00 eq) was dissolved in MeOH (114 mL), and Pd/C (0.37 g) was added thereto, followed by hydrogen purging (5 times) and stirring for 12 h at room temperature under a hydrogen atmosphere. The reaction was monitored by LCMS. A filter cake was obtained by filtration and washed with methanol (40 mL×2), and the filtrates were combined and rotary-dried to obtain 6.0 g yellow oil.

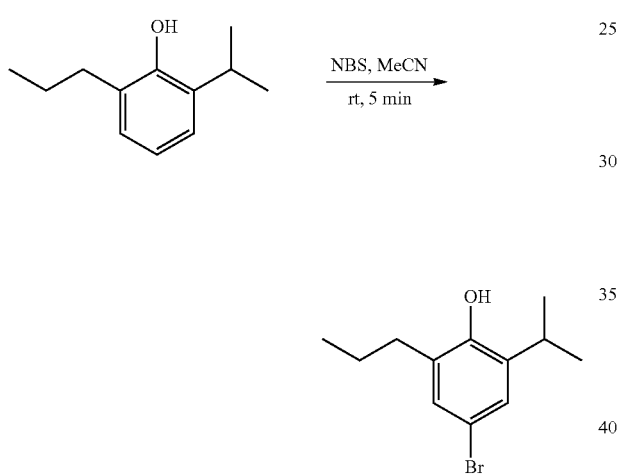

XA-2-3 (6 g, 50 mmol, 1.00 eq) was dissolved in anhydrous acetonitrile (70 mL), and NBS (3 g, 50 mmol, 1.00 eq) was added under stirring, followed by stirring for 5 minutes. The reaction was monitored with spots on a plate. The crude product obtained by low-temperature rotary drying was purified by column chromatography (petroleum ether/ethyl acetate-20:1, Rf-0.4) to obtain 6 g light yellow oil.

Step 7: 3,5-diisopropyl-3',5'-dipropyl-[1, 1'-biphenyl]-4,4'-diol (XA-1-7)

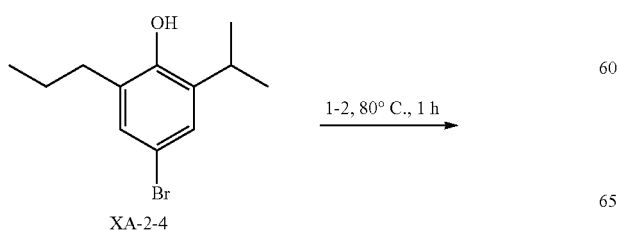

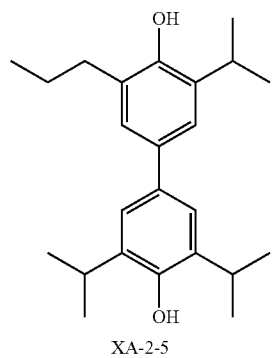 [SMILES: CCCc1cc(-c2cc(C(C)C)c(O)c(C(C)C)c2)cc(C(C)C)c1O]

XA-2-4 (2.49 g, 9.80 mmol, 1.00 eq) was dissolved in dioxane/water (30 mL/15 mL), and LiOH—H$_2$O (823 mg, 19.6 mmol, 2.00 eq), XA-1-2 (4.47 g, 14.7 mmol, 1.5 eq), and Pd(Amphos)$_2$Cl$_2$ (372 mg, 0.49 mmol, 0.05 eq) were sequentially added thereto, purged with nitrogen 5 times, stirred at room temperature for 5 minutes, and then heated and stirred at 80° C. for 1 hour. The reaction was monitored by LCMS. The reaction solution was diluted with ethyl acetate (90 mL), and washed with a saturated solution of sodium chloride (30 mL×3). The organic phase was dried over anhydrous sodium sulfate, and rotary-dried. The crude product was purified by column chromatography (petroleum ether/ethyl acetate=10:1, Rf-0.4) to obtain 1.8 g yellow solid (purity ~90%), which was further purified by high-pressure preparative liquid phase chromatography to obtain 1.5 g yellow solid as the product.

$^1$H NMR (500 MHz, Chloroform) δ 7.67 (s, 3H), 7.55 (s, 1H), 3.99 (s, 1H), 3.92 (s, 1H), 3.05 (s, 3H), 2.63 (s, 2H), 1.64 (s, 2H), 1.14 (s, 18H), 0.94 (s, 3H).

Example 3. Preparation of 3-isopropyl-3',5,5'-tripropyl-biphenyl-4,4'-diol

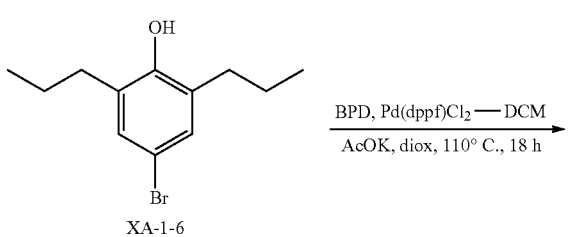

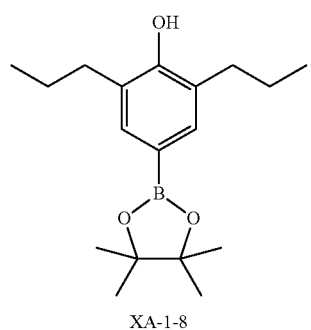

-continued

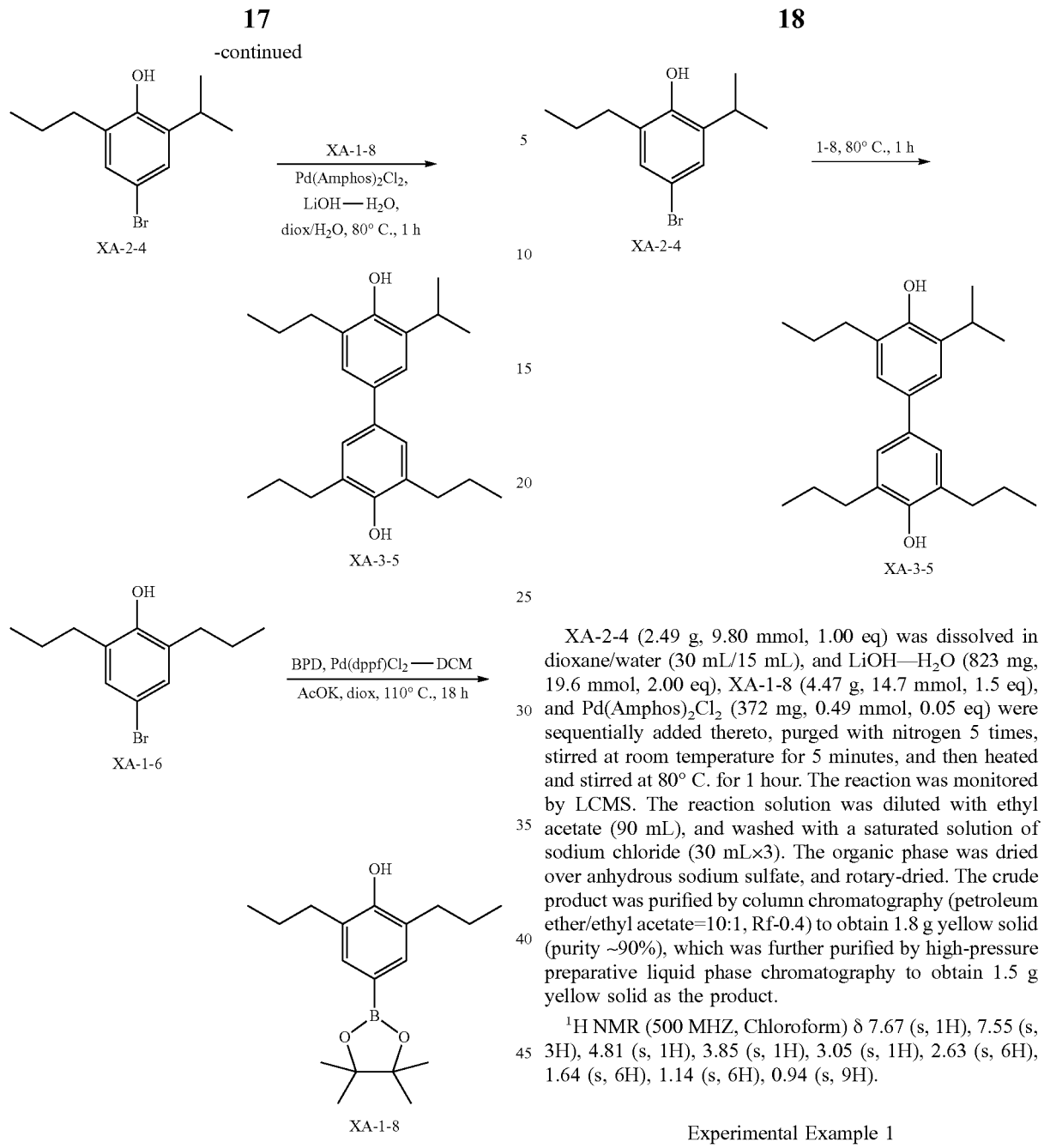

XA-1-6 (13.5 g, 52.5 mmol, 1.00 eq) was dissolved in dioxane/water (320 mL/32 mL), and then KOAc (25.7 g, 262.5 mmol, 5.00 eq), BPD (66.7 g, 262.5 mmol, 5.00 eq), and Pd(dppf)Cl$_2$ DCM complex (2.45 g, 3.00 mmol, 0.05 eq) were sequentially added, purged with nitrogen 5 times, stirred at room temperature for 5 minutes, and then heated and stirred for 18 h at 110° C. under nitrogen protection. The reaction was monitored with spots on a TLC plate until the reaction was complete. The reaction solution was rotary-dried. The resultant solid was diluted with ethyl acetate (300 mL) and washed with a saturated solution of sodium chloride (100 mL×3). The organic phase was dried over anhydrous sodium sulfate, and rotary-dried. The resultant solid was purified by column chromatography (petroleum ether/ethyl acetate=10:1, Rf=0.5) to obtain 24.5 g light yellow solid.

XA-2-4 (2.49 g, 9.80 mmol, 1.00 eq) was dissolved in dioxane/water (30 mL/15 mL), and LiOH—H$_2$O (823 mg, 19.6 mmol, 2.00 eq), XA-1-8 (4.47 g, 14.7 mmol, 1.5 eq), and Pd(Amphos)$_2$Cl$_2$ (372 mg, 0.49 mmol, 0.05 eq) were sequentially added thereto, purged with nitrogen 5 times, stirred at room temperature for 5 minutes, and then heated and stirred at 80° C. for 1 hour. The reaction was monitored by LCMS. The reaction solution was diluted with ethyl acetate (90 mL), and washed with a saturated solution of sodium chloride (30 mL×3). The organic phase was dried over anhydrous sodium sulfate, and rotary-dried. The crude product was purified by column chromatography (petroleum ether/ethyl acetate=10:1, Rf-0.4) to obtain 1.8 g yellow solid (purity ~90%), which was further purified by high-pressure preparative liquid phase chromatography to obtain 1.5 g yellow solid as the product.

$^1$H NMR (500 MHZ, Chloroform) δ 7.67 (s, 1H), 7.55 (s, 3H), 4.81 (s, 1H), 3.85 (s, 1H), 3.05 (s, 1H), 2.63 (s, 6H), 1.64 (s, 6H), 1.14 (s, 6H), 0.94 (s, 9H).

Experimental Example 1

1. Comparative Assay for the Distribution of Compound XA-1-7 and Dipropofol (3,3',5,5'-Tetraisopropyl Biphenyl-4,4'-Diol) in the Brain Tissue of Rats after Intravenous Administration 72 SD rats, each weighing 200 to 220 g, were randomly divided into 12 groups (6 per group at a time), and fasted for 12 hours before administration. Compound XA-1-7 or dipropofol was injected intravenously at a dose of 45 mg/kg, and the rats were sacrificed at 5 min, 15 min, 30 min, 1 h, 2 h, and 4 h after administration, immediately after which the brain tissue was removed, rinsed with ice-cold distilled water, blotted up, and cryopreserved at −40° C. The concentrations of Compound XA-1-7 or dipropofol in the brain tissue of rats at different time points after administration were measured by LC-MS/MS. The results are shown in Table 1 and FIG. 1.

TABLE 1

| | | Drug concentrations in brain tissue (ug/g) | | | | | |
|---|---|---|---|---|---|---|---|
| | | 5 min | 15 min | 30 min | 1 h | 2 h | 4 h |
| Compound 1 | Male average | 37.6 | 39.6 | 38.11 | 33.94 | 24.6 | 6.87 |
| | S.D. | 1.45 | 2.05 | 1.08 | 1.58 | 0.77 | 0.35 |
| Dipropofol | Total average | 12.8 | 24.1 | 32.5 | 26.6 | 17.9 | 5.52 |
| | S.D. | 1.19 | 1.61 | 1.99 | 1.24 | 0.61 | 0.51 |

At 5 minutes after intravenous injection, the concentration of Compound XA-1-7 in the brain tissue was about 3 times that of the dipropofol. The peak time of the concentration of Compound XA-1-7 in the brain tissue was at 15 minutes, while the peak time of the concentration of dipropofol was at 30 minutes after administration. The $AUC_{0-4\ h}$ of Compound XA-1-7 in the brain tissue was about 1.36 times that of the dipropofol.

The above results show that, after intravenous administration at the same dosage, the delivering speed into the brain and level in the brain of Compound XA-1-7 are significantly higher than those of the dipropofol.

2. In Vitro Target Affinity Test for $GABA_A$ Receptor

A radioligand ($[^{35}S]$ TBPS)-receptor competitive binding assay was conducted to evaluate the affinity of the test compound (10 uM) for the $GABA_A$ receptor. The results are shown in Table 2.

TABLE 2

| | Target | Species | Test concentration (uM) | IC50 |
|---|---|---|---|---|
| Dipropofol | GABAA, Chloride Channel, TBPS | Rat | 30, 10, 3, 1, 0.3 | 2.06 uM |
| Compound 1 | GABAA, Chloride Channel, TBPS | Rat | 30, 10, 3, 1, 0.3 | 1.82 uM |
| Compound 2 | GABAA, Chloride Channel, TBPS | Rat | 30, 10, 3, 1, 0.3 | 2.11 uM |
| Compound 3 | GABAA, Chloride Channel, TBPS | Rat | 30, 10, 3, 1, 0.3 | 2.69 uM |

The results show that Compounds XA-1-7, XA-2-5, and XA-3-5 all have high affinity for the $GABA_A$ receptor, and the affinity is comparable to that of the dipropofol.

3. Compound XA-1-7 and Dipropofol (3,3',5,5'-Tetraisopropyl Biphenyl-4,4'-Diol) Against PTZ-Induced Epileptic Seizure in Rats.

In this experiment, male SD rats (Xi'an Jiaotong University), each weighing 200 to 250 g, were given intravenous injections of dipropofol and Compounds XA-1-7, XA-2-5 and XA-3-5 at 45 mg/kg, and an equal volume of blank solvent. 1, 3, 5, 10, 15, 30, 60, 90, and 120 min after the intravenous administration, PTZ was injected intraperitoneally at 70 mg/kg to induce tonic-clonic epileptic seizures in the rats. There were 7 rats in each drug group at each time point. The seizure intensity of rats was graded according to the Racine grading standard, and seizures of grade III-V were recorded and given scores according to the seizure intensity: 5 points for level V, 4 points for level IV, 3 points for level III, and 0 points for levels below III. The seizure intensity for each group of animals was the sum of the scores of the 7 animals. The results are shown in Table 3.

The invention claimed is:

1. An allosteric enhancing compound of $GABA_A$ receptors or a prodrug thereof, wherein the compound is represented by formula (I), (II) and (III):

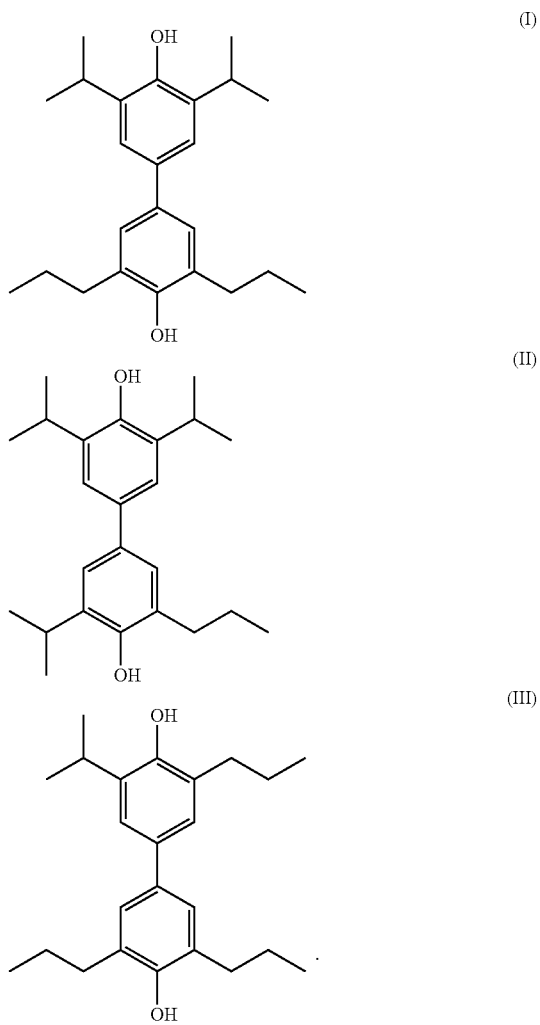

2. A pharmaceutical composition comprising a therapeutically effective amount of the allosteric enhancing compound of $GABA_A$ receptors or a prodrug thereof according to claim 1, and one or more pharmaceutically acceptable carriers and/or excipients.

* * * * *